US008637010B2

(12) United States Patent
Ny et al.

(10) Patent No.: US 8,637,010 B2
(45) Date of Patent: Jan. 28, 2014

(54) METHOD OF ACCELERATING WOUND HEALING BY ADMINISTRATION OF PLASMINOGEN

(75) Inventors: Tor Ny, Umea (SE); Jinan Li, Umea (SE); Sten Hellstrom, Umea (SE); Per-Olof Eriksson, Umea (SE)

(73) Assignee: Omnio Healer AB, Umeå (SE)

( * ) Notice: Subject to any disclaimer, the term of this patent is extended or adjusted under 35 U.S.C. 154(b) by 1722 days.

(21) Appl. No.: 11/253,972

(22) Filed: Oct. 18, 2005

(65) Prior Publication Data
US 2007/0041962 A1 Feb. 22, 2007

Related U.S. Application Data

(62) Division of application No. 10/237,144, filed on Sep. 5, 2002, now Pat. No. 7,067,492.

(60) Provisional application No. 60/317,643, filed on Sep. 6, 2001.

(51) Int. Cl.
*A61K 38/46* (2006.01)
*A61K 38/36* (2006.01)

(52) U.S. Cl.
USPC ...................... 424/94.64; 514/13.6

(58) Field of Classification Search
None
See application file for complete search history.

(56) References Cited

U.S. PATENT DOCUMENTS

| 5,925,350 | A | 7/1999 | Verheijen |
| 6,033,664 | A | 3/2000 | Verheijen |
| 6,043,407 | A | 3/2000 | Lodhi et al. |
| 6,124,273 | A | 9/2000 | Drohan et al. |
| 6,197,325 | B1 | 3/2001 | MacPhee et al. |
| 6,559,119 | B1 | 5/2003 | Burgess et al. |
| 7,067,492 | B2 | 6/2006 | Ny et al. |
| 7,202,066 | B2 * | 4/2007 | Ni et al. ............... 435/183 |

FOREIGN PATENT DOCUMENTS

| EP | 0 723 782 | 7/1996 |
| WO | WO 9013640 | * 11/1990 |
| WO | 0031244 | 6/2000 |
| WO | 0061179 | 10/2000 |

OTHER PUBLICATIONS

Lupinetti et al., "Cryoprecipitate-topical thrombin glue", J. Thorac. Cardiovasc. Surg. 90 : 502-505 (1985).*
McRoyan et al., "Antithrombin III, Plasminogen, Plasmin and Alpha-2-Antiplasmin in Donor Blood and Plasma Components", Annals or Clainical and Laboratory Science 15 (2) :165-170 (1985).*
Bannasch et al., "Treatment of Chronic Wounds with Cultured Autologous Keratinocytes as Suspension in Fibrin Glue", Zentralblatt fur Chirurgie 125 (Suppl. 1) : 79-81 (2000).*
Chung et al., "Protein Digestion and Absorption in Human Small Intestine", Gastroenterology 76 (6) : 1415-1421 (1979), abstract only.*
Bastian et al., "Proteolytic enzymes. HI. Circulating esterase activities after parenteral trypsin and chymotrypsin in rabbits", Proc. Soc. Exptl. Biol. And Med. 92 (4) : 800-803 (1956), abstract only.*
Li et al., "Plasmin/plasminogen is essential for the healing of tympanic membrane perforations", Thrombosis and Haemostasis, 96 (4) : 512-519 (2006).*
Kraft et al., "Ligneous conjunctivitis in a girl with severe type I plasminogen deficiency", Graefe's Arch. Clin. Exp. Opthalmol. 238 : 797-800 (2000).*
Hatton et al., "Behavior of plasminogen at the luminal surface of the normal and deendothelialized rabbit aorta in vivo and in vitro", Blood 71 : 1260-1267 (1988).*
Romer et al., Nature Medicine, 1996, 2(3): 287-292.
Laurent et al., Arch Otolaryngol Head Neck Surg., 1988, 114:1435-1441.
Fina et al., Laryngoscope, 1993, 103;804-809.
Hellstrom et al., In: Fidia Research Series, vol. 8, Liviana Press, Padova 1989, pp. 181-188.
Creemers, E. et al.: Disruption of the Plasminogen Gene in Mice Abolishes Wound HEaling after Myocardial Infarction, American Journal of Pathology, 2000,156(6):1865-1873.
Kao et al., Healing of Corneal Epithelial Defects in Plasminogen- and Fibrinogen-Deficient Mice, Investigative Opthalmology & Visual Science, 1998, 39(3):502-508.
Hamann, A new material for closure of traumatic perforation of the tympanic membrane, Laryngo-Rhino-Otologie, 1990, 69(3):173.
Dileo et al., Fibrin-Glue-Reinforced Paper Patch Myringoplasty of Large Persistent Tympanic Membrane Perforation in the Guinea Pig, ORF, vol. 58, No. 1, 1996, pp. 27-31.
Strauss et al., Does Human Fibrin Glue Improve Results in Tympanoplasty, Laryngologie, Rhinologie, Otologie, vol. 63, No. 12, Dec. 1984, pp. 615-617.
Hagen, Fibrinolysis Treatment with Rt-Pa Recombinant Tissue Type-Plasminogen Activator in Sudden Hearing Loss Hemorheologic and Therapeutic Effects, Laryngo-Rhino-Otologie, vol. 70, No. 7, 1991. pp. 353-358.
IP, CGP 1998A—Effects on Hormone-Dependent and -Independent Tumors. Potential for Treatment of Breast and Prostate Cancer, Proc. Int. Congr. Chemother., 1983;16:284/192-284/195.
Final Office Action received for U.S. Appl. No. 11/947,952, mailed on Feb. 1, 2012, 7 pages.
Non-Final Office Action received for U.S. Appl. No. 11/947,952, mailed on Jul. 6, 2011, 8 pages.
Non-Final Office Action received for U.S. Appl. No. 11/947,952, mailed on Jul. 26, 2013, 4 pages.
Levenson, et al., "Nature and appearance of protein digestion products in upper mesenteric blood", Proc. Soc. Exptl. Biol. and Med., vol. 101, No. 1, abstract only, 1959, pp. 178-18D.

* cited by examiner

*Primary Examiner* — Sandra Saucier
(74) *Attorney, Agent, or Firm* — Morrison & Foerster LLP

(57) ABSTRACT

The present invention relates to the use of plasminogen and plasmin as agents for enhancing healing of tympanic membrane perforations or other wounds, and for reducing scars or necrotic tissue forming during wound healing. The invention also relates to a method for screening of compounds which enhance wound healing by evaluating the healing of tympanic membrane perforations in an animal model.

4 Claims, 1 Drawing Sheet

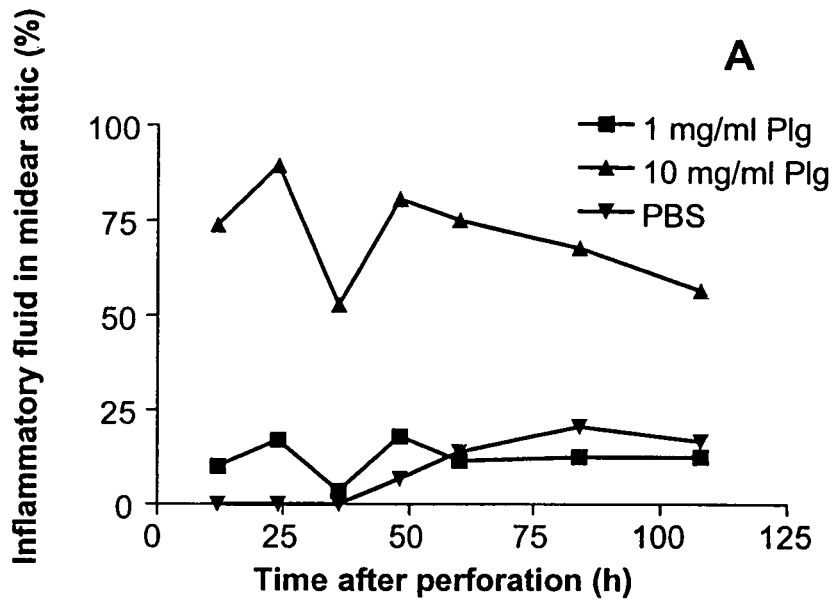
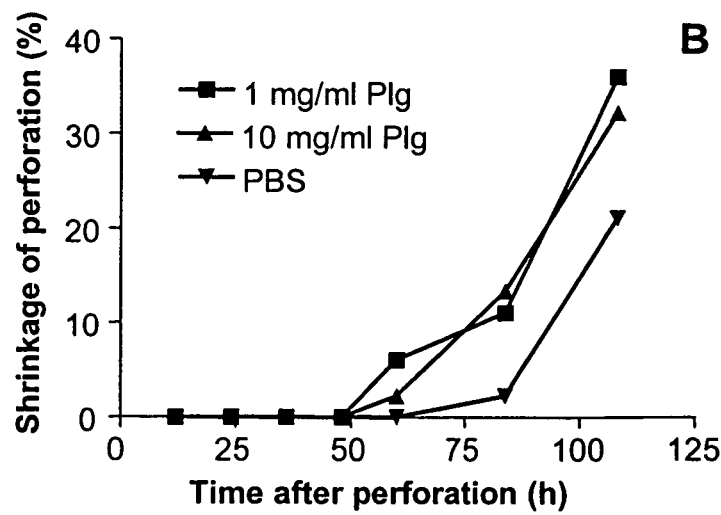

METHOD OF ACCELERATING WOUND HEALING BY ADMINISTRATION OF PLASMINOGEN

This application is a Divisional of U.S. Ser. No. 10/237,144, filed Sep. 5, 2002, no allowed, which claims benefit under 35 U.S.C. §119(e) of U.S. Provisional Application No. 60/317,643, filed Sep. 6, 2001.

FIELD OF THE INVENTION

This invention relates to wound healing processes. In particular, the invention relates to novel methods of promoting the healing or closure of perforated tympanic membranes or wounds, as well as methods for minimizing scar formation and removing necrotic tissue. The invention also relates to animal models for studying wound-healing processes, and screening methods for identifying and evaluating drugs and treatment methods for enhancing healing of perforated tympanic membranes or wounds.

BACKGROUND

Slow or improper wound healing compromises the quality of life for large numbers of people. One particular type of wound healing where problems can occur is the healing of tympanic membrane (eardrum) perforations. Although the majority of perforations will heal spontaneously, and are closed by proliferating keratinizing squamous epithelium advancing ahead of an ingrowing connective tissue, some perforations do not heal, frequently resulting in loss of hearing or other complications. It is still an open question why some perforations heal, whereas others stay patent. In addition, every year in the United States more than 1.25 million people suffer from burns, and 6.5 million have chronic skin ulcers caused by pressure, venous stasis, or diabetes mellitus.

Wound healing is a dynamic tissue remodeling process involving the formation of a matrix rich in fibrin and fibronectin in the wound field, infiltration of neutrophils and macrophages, proliferation of epidermal keratinocytes at the wound edges and their migration through the provisional matrix, formation of granulation tissue containing newly developed vessels and migrating inflammatory cells and fibroblasts, and wound contraction. Wound healing studies of skin suggest that proteases play important roles in several steps. It is well documented that the degradation of the extracellular matrix (ECM) that takes place during wound healing and other ECM remodeling processes is dependent on the action of a variety of proteolytic enzymes secreted by inflammatory cells, as well as by stromal tissue cellular elements. Many different proteinases are thought to contribute to matrix remodeling during wound healing (Saksela and Rifkin, Annu. Rev. Cell Biol. 4, 93-126 (1988)). However, the precise mechanisms responsible for this process, and how they are regulated, are poorly understood.

The Plasminogen-Activation System

The plasminogen-activation system is a versatile, temporally controlled enzymatic system in which plasminogen is activated to the proteolytic enzyme plasmin by either of the two physiological plasminogen activators (PAs), tissue-type plasminogen activator (tPA) and urokinase-type plasminogen activator (uPA). Activation of this system is initiated by the release of tPA or uPA by specific cells in response to external signals and leads to a locally expressed extracellular proteolytic activity (Vassalli et al. J. Exp. Med. 159, 1653-1668 (1984); Saksela & Rifkin, 1988, supra). The PA-system is also regulated by specific inhibitors directed against PAs and plasmin, including PA-inhibitor type 1 (PAI-1), PA-inhibitor type 2 (PAI-2), protease nexin 1 (PN-1) and α2-anti-plasmin (Saksela & Rifkin, 1988, supra; Ny et al., Thromb Res. 71(1): 1-45 (1993)). All of these inhibitors, which belong to the serpin family, are suicide inhibitors that are cleaved by cognate protease (Wilczynska et al., J Biol Chem. 270(50):29652-5 (1995); Wilczynska et al., Nat Struct Biol. 4(5):354-7 (1997)). The most important feature of the PA-system is the amplification achieved by the conversion of plasminogen resulting in the formation of plasmin.

PAs have been found to be present in wound edges, along with several types of matrix metalloproteinases (MMPs), including interstitial collagenase (MMP-1), stromelysin-1 (MMP-3), and the latent forms of gelatinase A (MMP-2) and gelatinase-B (MMP-9). The expression of both PAs and MMPs is induced by inflammatory mediators and cytokines, indicating that the two enzyme systems may act in concert. MMPs are known to be synthesized as latent precursor enzymes that can be activated by limited proteolysis, but the exact mechanism by which this activation takes place in vivo is largely unknown. Plasmin is one of the factors proposed to be involved in the activation of some subclasses of metalloproteinases (Lijnen, Thromb Haemost 86(1):324-33 (2001)).

A number of reports have indicated that the expression or activation of MMPs, tissue inhibitors of metalloproteinases (TIMPs), PAs and PA-inhibitors are altered in wound healing processes, and there has also been indications that plasmin plays a role in skin wound healing (Romer et al., Nat. Med. 2:287-292 (1996)). Moreover, U.S. Pat. Nos. 5,925,350 and 6,033,664 to Verheijen describe the use of uPA or tPA to improve wound healing of slow- or non-healing wounds. In these studies, it was noted that the improvement mechanism was not associated with fibrinolytic activity or necrotic tissue removal. Specific strategies for improving tympanic membrane healing have also been proposed, using topical application of high concentrations of hyaluronan (Laurent et al., Arch Otolaryngol Head Neck Surg 114:1435-1441 (1988)) or basic fibroblast growth factor (bFGF; Fina et al., Laryngoscope 103(7):804-809 (1993)).

While the understanding of wound healing and the various mechanisms regulating it is improving, and promising treatment strategies have been proposed, the healing of slow- or non-healing tympanic membrane perforations or other wounds remain a medical as well as social problem. There is thus a need in the art for new and improved methods for accelerating wound healing processes, such as healing of tympanic membrane perforations, burns and skin ulcers, removing any necrotic tissue, and minimizing scar formation. There is also a need for new screening methods by which to identify and evaluate drugs that can be used in such treatment methods. The invention addresses these and other needs in the art.

SUMMARY OF THE INVENTION

The present invention provides a new method for improving the healing of tympanic membrane perforations, or minimizing scar formation during healing, by administration of plasminogen.

Accordingly, the invention provides a method of promoting healing of a tympanic membrane perforation in a subject in need of such treatment, which comprises administering to the subject a composition containing an effective amount of plasminogen for promoting healing of the tympanic membrane perforation. Preferably, the subject is a human, and the plasminogen is human plasminogen. The composition may further comprise a pharmaceutically acceptable carrier, and can be in the form of an aqueous solution, a gel, a lotion, a balm, a powder, a paste, a bandage, a wound dressing, or another suitable delivery vehicle. The plasminogen can be administered topically or systemically. In the case of topical administration, the administered composition may comprise from about 0.05 mg to about 10 mg plasminogen, preferably from about 0.5 to about 5 mg plasminogen. The composition may promote healing by accelerating the healing of the perforation, reducing necrotic tissue, and reducing the formation of scar tissue in the wound area. In one embodiment, the plasminogen administration is repeated at least once, preferably at least once every day.

The invention also provides a method of reducing scar formation from a healing wound in a subject in need of such treatment, which comprises administering to the subject a composition containing an effective amount of plasminogen for reducing scar formation. The plasminogen can, for example, reduce fibrin deposition. The subject is preferably a human subject, and the plasminogen is preferably human plasminogen. In one embodiment, the plasminogen is administered topically, and the composition can comprise from about 0.5 mg to about 5 mg plasminogen per square centimeter wound area.

The invention also provides for a method of accelerating wound healing in a patient in need of such treatment, which comprises administering to the patient a composition containing an effective amount of plasminogen to promote healing of the wound. Optionally, the wound is a chronic wound. The subject may be a human subject, in which case the plasminogen is preferably, although not necessarily, human plasminogen. In case the plasminogen is administered topically, it may be administered so that from about 0.5 mg to about 5 mg plasminogen is applied per square centimeter wound area.

The invention also provides for a method of accelerating wound healing in a patient in need of such treatment, which comprises administering to the patient a composition containing an effective amount of plasmin to promote healing of the wound. The wound may, optionally, be a chronic wound. In one embodiment, the subject is a human subject, and the plasmin is human plasmin. If the composition is administered by topical administration, the composition can comprise, for example, from about 0.005 mg to about 0.5 mg plasminogen per square centimeter wound area.

The invention also provides for a method of reducing necrotic tissue formation in a healing wound in a subject in need of such treatment, which comprises administering to the subject a composition containing an effective amount of plasminogen for reducing necrotic tissue formation. Optionally, the plasminogen reduces fibrin deposition. In one embodiment, the subject is a human subject, and the plasminogen is human plasminogen. If administered topically, the composition may be applied in an amount corresponding to, for example, from about 0.5 mg to about 5 mg plasminogen per square centimeter wound area.

The invention also provides a method of identifying an agent that is useful in promoting wound healing, which method comprises: (i) administering a test agent to an animal having a tympanic membrane perforation; (ii) evaluating at least one of the extent of healing, necrotic tissue formation, and scar formation of the tympanic membrane perforation; (v) comparing the extent of healing, necrotic tissue formation, or scar formation to a control value; and (vi) selecting any test agent for which the extent of healing is higher or the necrotic tissue or scar formation lower than the control value as an agent useful in promoting wound healing. The animal can, for example, be a wild-type animal or a transgenic animal lacking endogenous expression of plasminogen, preferably selected from a mouse or a rat. In one embodiment, the test agent is administered by topical administration. The control value may be, for example, the extent of healing or scar or necrotic tissue formation in a second animal, to which the test agent has not been administered.

The above features and many other advantages of the invention will become better understood by reference to the following detailed description when taken in conjunction with the accompanying drawings.

BRIEF DESCRIPTION OF THE DRAWINGS

FIGS. 1A and 1B. Time course of (A) inflammatory reaction in the mid-ear cavity and (B) shrinkage of perforation, after tympanic membrane perforation in wild-type rats. Fifty µl plasminogen (50 µg (1 mg/ml) -■-; or 0.5 mg (10 mg/ml) -▲-) or control (PBS, -▼-) solution was administered after perforation, and thereafter every 24 hours.

DETAILED DESCRIPTION OF THE INVENTION

The present invention relates to healing of perforated tympanic membranes, and to healing of wounds. The invention is also applicable to diseases and conditions characterized by degeneration or poor healing of extracellular matrix structures, particularly the keratinized tissue such as, e.g., the tympanic membrane. Other abnormal wound healing processes include diabetic ulcers, keloids, hypertrophic scars, and the application of skin substitutes.

The invention is based, in part, on the discovery that in the absence of plasminogen, the wound healing process does not progress properly, showing that plasminogen plays a pivotal role in the healing of wounds, particularly in the case of tympanic membrane perforations (see Examples and Table 1). As shown by the Examples, healing of tympanic membrane perforations was dramatically altered and abnormal in mice lacking plasminogen as compared to wild-type controls and other transgenic models (see Table 1). In plasminogen deficient mice, tympanic membrane perforations did not heal properly during the 144-day test period during which healing was monitored, resulting in an abnormal tympanic membrane. It was also found that plasminogen-deficient mice reverted to a normal healing process following injection of human plasminogen. (see Examples 2 and 5), and that wild-type rats displayed enhanced tympanic membrane healing after administration of plasminogen (Example 6). In addition, experiments showed that uPA, but not tPA, may also play some role in normal wound healing, in that uPA appeared to be needed for the removal of fibrin depositions (Example 3 and 4). However, in no animal model was the lack of normal healing more apparent than in plasminogen-deficient mice, indicating that plasminogen plays a more essential and probably different role during wound healing than uPA. Without being bound to any specific theory, the present findings supports that the inability to proper healing may be caused by a defect in the inflammatory response, keratinocyte migration, or matrix remodeling events during the healing process.

As demonstrated by the results in Table 1, uPA, tPA, and plasminogen play distinct roles in the wound healing process, with plasminogen playing a pivotal role. In addition, as shown in the Examples, removal of necrotic tissue and fibrin are critically dependent on the presence or administration of plasminogen/plasmin rather than tPA or uPA.

TABLE 1

Comparison of Time of Healing and Appearance of Healed Tympanic Membrane Tissue
in Wild-Type, uPA-Deficient, tPA-Deficient, and Plasminogen-Deficient Mice

| Genotype | Day of healing | Healing Pattern | Necrosis | Fibrin deposition |
|---|---|---|---|---|
| Wild-type | 8.7 ± 2.4 | Normal healing | No | No |
| tPA $^{-/-}$ | 9.0 ± 2.4 | Apparently normal healing | No | No |
| uPA $^{-/-}$ | 11.0 ± 1.7 (7/8 mice healed at day 11) | Healed area contains ruffled surface and cobble-stone-like tissue deposits | No | Spots of fibrin depositions at healed area. |
| Plg $^{-/-}$ | — (0/8 mice healed at day 144) | Tympanic membrane covered by whitish tissue, and is thick and non-transparent | Necrosis becomes apparent from day 16 and onwards | Extensive fibrin deposition that completely covers tympanic membrane surface |

Accordingly, plasminogen could be used in the treatment of wound healing diseases, as well as for acceleration strategies for tympanic membrane and wound healing, treatment of conditions or diseases affecting healing of disrupted epidermal tissues, methods for reducing scar formation or necrotic tissue accumulation or formation, as well as screening methods for drugs to be used in such treatments. The administration of plasminogen can also minimize scar formation or necrotic tissue accumulation in tympanic membranes or other epidermal tissues during wound healing. For example, plasminogen can be applied in conjunction with plastic surgery to reduce the appearance of, or prevent, the formation of residual scars, fibrin deposits, or necrotic tissue. Also, plasminogen can be applied onto ulcers or burns to improve healing.

In addition, the method of the invention can be used for improving wound healing in conditions of local or systemic deficiency of plasminogen, or to improve the healing of non- or slow-healing wounds. Notably, as shown in Example 5, restoration of plasminogen weeks after injury can diminish the accumulated extracellular matrix and restart normal healing, thus showing that plasminogen can be applied for treatment of chronic wounds such as ulcerations and bedsores.

Alternatively, plasmin itself could be used in the treatment of wound healing diseases, as well as for acceleration strategies for tympanic membrane and wound healing, treatment of conditions or diseases affecting healing of disrupted epidermal tissues, or methods for reducing scar formation or necrotic tissue accumulation or formation. The administration of plasmin can also minimize scar formation or necrotic tissue accumulation in tympanic membranes or other epidermal tissues during wound healing. For example, plasmin can be applied in conjunction with plastic surgery to reduce the appearance of, or prevent, the formation of residual scars, fibrin deposits, or necrotic tissue. Also, plasmin can be applied onto ulcers, bedsores, or burns to improve healing.

The compositions of the invention can be administered topically, by injection, or by intravenous infusion. Preferably, although not necessarily, the administration is local, i.e., in some proximity to the wound. When the plasminogen or plasmin is administered by injection (e.g., intravenously, subcutaneously, intramuscularly), it is advantageously prepared as a solution of the material in a pharmaceutically acceptable liquid, such as, e.g., isotonic saline. In a preferred embodiment, plasminogen or plasmin is administered locally to attain a high concentration, for example, at least 200 µg/ml plasminogen or at least 20 µg/ml plasmin, in the perforation or wound area. For topical administration, the plasminogen or plasmin composition may, for example, be part of a gel, lotion, balm, paste, spray, powder, bandage, or wound dressing. For accelerating healing of a tympanic membrane perforation, the composition is preferably administered via the outer ear canal, by, e.g., a spray delivered to the area of the perforation, or by adding plasminogen or plasmin solution drop-wise. Devices for delivering compositions by spray are known in the art, and is described in, e.g., U.S. Pat. No. 6,027,712. Strategies such as administering the plasminogen/plasmin by spray, as well as by gel or paste, or a topically administered solution, can also be used for treating wounds in the oral cavity. For acceleration of wound healing, plasminogen or plasmin can be present in a wound dressing applied onto the wound, from which it is transferred to the wound area. In another embodiment, the composition comprises a compound that mimics plasminogen activity or plasmin activity, such as a plasminogen/plasmin fragment or mutant, or another molecule with similar activity.

The invention also provides for screening methods to identify compounds useful for improving wound healing in an animal model. The screening method is preferably based on a tympanic membrane perforation animal model which provides detailed functional description with respect to wound healing, thereby enabling efficient screening, identification and characterization of new chemical entities, pharmacological effects, and novel drug targets involved in the healing of tympanic membrane perforations and other wound healing diseases. Accordingly, a wound can be inflicted in a wild-type or plasminogen-deficient animal, and a test compound administered to the animal via a predetermined route. Wound healing in the animal and/or plasminogen levels in the wound area can then be compared to a control value such as, e.g., wound healing in a wild-type animal or an animal to which the test agent has not been administered, to evaluate whether the test compound improved the rate of healing or reduced necrotic tissue or scar formation. In one embodiment, the animal is a knock-out mouse lacking one or both alleles of plasminogen. As a control model, or for further testing of the agent identified, a model in which wild-type components of the plasminogen activation system is normally expressed, or, alternatively, a transgenic animal model in which one or more wild-type proteins have been replaced with the corresponding human or non-human homologs, can be used.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

"Tympanic membrane" and "eardrum" are used interchangeably herein.

A "tympanic membrane perforation" is an opening in the tympanic membrane usually caused by trauma. There are at least four general categories: compression injuries (the most common and usually the result of a blow to the ear); instrumentation injuries (the second most common, usually inadvertent, caused often by cotton swabs or bobby-pins); burn-slag injuries (frequently seen in industry, from hot metal from machines or welding); and blast injuries (usually seen during war or bombings). Infection can cause delayed healing of the tympanic membrane, and persistent perforation is usually a manifestation of tubotympanitis, an inflammation of the eustachian tube and tympanic cavity (middle ear).

A "wound" is a break or discontinuity in the structure of an organ or tissue, including epithelium, connective tissue, and muscle tissue, caused by an external agent. Examples of wounds include, but are not limited to, skin wounds, bruises, ulcerations, bedsores, grazes, tears, cuts, punctures, psoriasis wounds, tympanic membrane perforations, and burns. A particular type of wounds are those that are a consequence of plastic surgery procedures.

"Topical" and "topical application" refer to non-systemic, local, administration of an active ingredient. Thus, topical application can refer to application of an active ingredient to the external surface of a wound.

"Plasminogen" herein includes endogenously occurring mammalian plasminogen, allelic plasminogen, function-conservative derivatives of plasminogen, functionally active plasminogen fragments, and mammalian plasminogen homologs. Optionally, a plasminogen composition may contain more than one type, derivative, or homolog of plasminogen. Preferably, the type of plasminogen to be used in a composition to be administered to a subject is endogenous to the species of the subject. A preferred compound is plasminogen purified from a biological source, e.g., recombinantly produced human plasminogen, or purified human plasminogen, which is available from, for example, Biopool AB (Umeå, Sweden). One preferred human plasminogen has the amino acid sequence of GenBank Accession No. PLHU (GI: 625234) (SEQ ID NO: 1).

"Plasmin" herein includes endogenously occurring mammalian plasmin, allelic plasmin, function-conservative derivatives of plasmin, functionally active plasmin fragments, and mammalian plasmin homologs. Optionally, a plasmin composition may contain more than one type, derivative, or homolog of plasmin. Preferably, the type of plasmin to be used in a composition to be administered to a subject is endogenous to the species of the subject. A preferred compound is plasmin purified from a biological source, e.g., recombinantly produced human plasmin, or purified human plasmin.

"Function-conservative variants" are proteins in which a given amino acid residue has been changed without altering overall conformation and function of the protein, including, but not limited to, replacement of an amino acid with one having similar properties (such as, for example, acidic, basic, hydrophobic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, more preferably at least 85%, even more preferably at least 90%, and still more preferably 95%, and which has the same or substantially similar properties or functions as the native or parent protein or enzyme to which it is compared.

A "subject" herein includes both human and non-human animals. Non-human animals include, without limitation, mammals, laboratory animals such as mice, rats, rabbits, hamsters, guinea pigs, etc.; domestic animals such as dogs and cats; and farm animals such as sheep, goats, pigs, horses, and cows. A non-human animal of the present invention may be a mammalian or non-mammalian animal; a vertebrate or an invertebrate.

"Treatment" of a subject, or "treating" a subject for a disease or condition herein means reducing or alleviating clinical symptoms of the disease or condition such as impaired or slow wound-healing.

"Promote", "enhance", or "improve" tympanic membrane or wound healing generally means increasing the speed by the which the wound or perforation heals or reducing the extent of residual scar or necrotic tissue during or after healing of the wound or perforation.

A "control", "control value" or "reference value" in an assay is a value used to detect an alteration in, e.g., the healing of a perforated tympanic membrane or skin wound, or any other assays described herein. For instance, when studying healing of a tympanic membrane perforation, the inhibitory/stimulatory effect of an agent can be evaluated by comparing the healing of a wound or perforation to that of a control. The control or reference may be, e.g., a predetermined reference value, or may be determined experimentally. For example, in such an assay, a control or reference may be the healing of a similar wound or perforation in an animal not exposed to the drug or active agent, or an animal treated with the same drug or active agent which does not have impaired wound healing capability An "effective amount" or a "therapeutically effective amount" means an amount that increases the local and/or systemic concentrations of plasminogen, and/or enhances wound healing. For example, an effective amount of an active agent can be an amount that results in a local (in the perforation, wound, or scar area) or systemic level of plasminogen that exceeds 200 microgram/ml. Alternatively, an effective amount of an agent is an amount that results in a faster healing of a perforation or wound than in the absence of the agent, or a reduced scar or necrotic tissue formation than in the absence of the agent. An effective amount could also mean an amount or dose sufficient to increase the local and/or systemic levels of plasminogen, e.g., to about 10 percent, preferably by about 50 percent, and more preferably by about 100 percent of the level found before administration of the active agent or drug. Alternatively, an effective amount of plasminogen is an amount corresponding to about 5 µg to about 50 mg, preferably about 0.05 mg to about 10 mg, and, even more preferably, from about 0.5 mg to about 5 mg plasminogen per square centimeter in the wound area. A therapeutically effective amount can ameliorate or present a clinically significant response in a subject, in that, e.g., tympanic membrane perforation or wound healing is promoted, or scar formation reduced. Alternatively, a therapeutically effective amount is sufficient to improve a clinically significant wound-healing or scar formation condition in the host.

As used herein, "about" or "approximately" shall mean within 50 percent, preferably within 20 percent, more preferably within 5 percent, of a given value or range.

A value which is "substantially different" from another value can mean that there is a statistically significant difference between the two values. Any suitable statistical method known in the art can be used to evaluate whether differences are significant or not. A "statistically significant" difference means a significance is determined at a confidence interval of at least 90%, more preferably at a 95% confidence interval.

In accordance with the present invention there may be employed conventional molecular biology, microbiology, and recombinant DNA techniques within the skill of the art. Such techniques are explained fully in the literature. See, e.g., Sambrook et al. (Molecular Cloning—A Laboratory Manual, Cold Spring Harbor Laboratory Press, 1989); Glover (DNA Cloning: A Practical Approach, Volumes I and II, 1985); Hames and Higgins (Nucleic Acid Hybridization, 1985); Hames and Higgins (Transcription And Translation, 1984); Freshney (Animal Cell Culture, 1986); Perbal (A Practical Guide To Molecular Cloning, 1984); and Ausubel et al. (Current Protocols in Molecular Biology, John Wiley & Sons, Inc., 1994).

Abbreviations used in the present disclosure include the following:
uPA=Urokinase-type plasminogen activator;
PA=Plasminogen activator;
MMP=Matrix metalloproteinase;
TIMP=Tissue inhibitor of metalloproteinase;
tPA=Tissue-type plasminogen activator;
Plg=Plasminogen
ECM=Extracellular matrix Improvement of Wound Healing According to the invention, wound healing is improved by providing or enhancing the levels of plasminogen. This may be accomplished in several different ways. For instance, a patient may be treated with an effective amount of an active agent such as, e.g., a drug, hormone, cytokine, antibody, or another compound that up-regulates the expression of plasminogen; reduces the degradation of plasminogen; or increases the local or systemic levels of plasminogen or a plasminogen homolog or derivative. Nucleic acids encoding plasminogen may also be administered for therapeutic purposes.

In a preferred embodiment, a substantially pure preparation of human plasminogen is used. Plasminogen may be purchased in purified form, or produced by purifying the component from humans or other animals, or by recombinant production in host cells, including prokaryotic host cells such as S. cerevisiae or E. coli, and, more preferably, mammalian host cells such as CHO cells. The plasminogen may be wild-type human, a mammalian homolog, or modified/mutated. In particular, fragments of the component which retain at least a part of the desired activity of the full-length component may be used Applications The method of the invention may be used to accelerate the healing of a tympanic membrane or other wound in animals including, but not limited to, vertebrates such as humans and domestic animals, including dogs, cats, and horses. In addition, plasminogen may be used in a clinical applications to reduce scar tissue formation and necrotic tissue in a wound area, and to enhance removal of tissue debris.

In one embodiment, the method of the invention is applied for enhancing the healing of a perforated tympanic membrane in a human subject. The human or non-human subject may or may not suffer from a condition which impairs or slows down the healing of the tympanic membrane perforation.

In another embodiment, the method of the invention provides a method for accelerating the healing of a wound in a subject. The subject may or may not suffer from a condition which is associated with the appearance of wounds, or from a condition that affects wound healing, such as diabetes (e.g., diabetic ulcer keloids), chronic wounds such as ulcers or bedsores.

Since the method of the invention not only increases the wound healing rate, but also improves the quality of the wounds, i.e., reduces the appearance of scars and the appearance of necrotic tissue, a composition which enhances the levels of plasminogen at least in the wound area can be administered to any patient to reduce scar formation. In a particular embodiment, the subject is a human which plans to undergo, is undergoing, or has undergone, plastic surgery or application of a skin substitute. In such a case, a composition comprising plasminogen can be applied or administered both prior to and/or after surgery.

Furthermore, the administration of plasminogen can restart a normal wound healing pattern in situations of impaired wound healing. Without being bound to any particular theory, besides fibrinolysis, elevated plasminogen levels may lead to increased plasmin, which may initiate a wound healing process through activation of cytokine pathways.

Compositions and Treatments

The invention provides plasminogen compositions, which, when administered in an effective amount, results in an increased plasminogen level in the wound area of a subject and thereby improved healing of a tympanic membrane perforation or other wound.

For example, for acceleration of tympanic membrane healing, a composition comprising about 5 µg to about 50 mg, preferably about 0.05 mg to about 10 mg, and, even more preferably, from about 0.5 mg to about 5 mg plasminogen, including a plasminogen homolog or derivative, can be applied to the area surrounding a tympanic membrane perforation. Alternatively, about 10-50 µl of a 1 mg/ml plasminogen solution, or the corresponding amount delivered in another suitable formulation, can be applied. For acceleration of the healing of wounds in general, a plasminogen composition can be applied so that the amount of plasminogen per each square centimeter ($cm^2$) of the wound area comprises about 5 µg to about 50 mg, preferably about 0.05 mg to about 10 mg, and, even more preferably, from about 0.5 mg to about 5 mg plasminogen, including a plasminogen homolog or derivative.

Alternatively, plasminogen is administered so that a locally high concentration of plasminogen is achieved in the tympanic membrane perforation or wound area of a subject, e.g., a human patient. In a preferred embodiment, the administration of an effective amount of the active agent results in a plasminogen concentration of at least about 200 µg/ml in the perforation or wound area. In yet another preferred embodiment, the administration of an effective amount of the active agent results in a plasminogen concentration of at least about 200 µg/ml in the perforation or wound area. In still another preferred embodiment, the concentration of plasminogen resulting from administration of an effective amount of an active agent is from about 2 μg/ml up to about 2 mg/ml, more preferably at least 200 μg/ml. The concentration of plasminogen in human plasma is about 200 microgram per ml.

In the case of plasmin compositions, for acceleration of tympanic membrane healing, a composition comprising about 0.05 μg to about 5 mg, preferably about 0.5 mg to about 1 mg, and, even more preferably, from about 5 μg to about 0.5 mg plasminogen, including a plasmin homolog or derivative, can be applied to the area surrounding a tympanic membrane perforation. Alternatively, about 10-50 μl of a 1 mg/ml plasmin solution, or the corresponding amount delivered in another suitable formulation, can be applied. For acceleration of the healing of wounds in general, a plasmin composition can be applied so that the amount of plasmin per each square centimeter ($cm^2$) of the wound area comprises about 0.05 μg to about 5 mg, preferably about 0.5 μg to about 1 mg, and, even more preferably, from about 5 μg to about 0.5 mg plasmin, including a plasmin homolog or derivative.

Accordingly, plasminogen or plasmin may be formulated into pharmaceutical compositions for administration to subjects in a biologically compatible form suitable for administration in vivo, e.g., by topical administration, injection, or infusion. By biologically compatible form suitable for administration in vivo is meant a form of the substance to be administered in which any toxic effects are outweighed by the therapeutic effects. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual. Dosage regima may be adjusted to provide the optimum therapeutic response. For example, more than one divided doses may be administered daily or the dose may be proportionally reduced as indicated by the exigencies of the therapeutic situation.

If desired, other active ingredients may also be applied in conjunction with plasminogen or plasmin treatment of a perforation or wound. Such active ingredients include, but are not limited to, mammalian PAs such as human tPA or human uPA, or bacterial PAs such as streptokinase.

The active substance may be administered in a convenient manner such as by injection (subcutaneous, intravenous, etc.), inhalation, spray, topical or transdermal application, or rectal administration. Depending on the route of administration, the active substance may be coated in a material to protect the compound from the action of enzymes, acids and other natural conditions that may inactivate the compound. Thus, suitable routes of administration include topical, intravenous, intramuscular, intradermal, rectal, and intravaginal administration. A preferred administration route is topical administration. In the case of tympanic membrane perforations, the active agent can be administered via the outer ear canal. The vessels that support the tympanic membrane stops at the border of the membrane. Accordingly, blood and blood components such as oxygen, nutrition and plasminogen only reaches the tympanic membrane by diffusion.

The compositions described herein can be prepared by methods known per se for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Mack Publishing Company, Easton, Pa., USA 1985). On this basis, the compositions include, albeit not exclusively, solutions of the substances or compounds in association with one or more pharmaceutically acceptable vehicles or diluents, and contained in buffered solutions with a suitable pH and iso-osmotic with the physiological fluids.

Examples of vehicles that may be used in delivering the plasminogen or other compositions according to the invention include, but are not limited to, injectable dosage forms, infusions, gel, pastes, balms, waxes, lotions, skin creams, and various other formats for topical administration known in the art. The compositions may also be delivered locally in the form of a powder or solution sprayed onto the wound area. Alternatively, the compositions of the invention may be present in wound dressings, pads, band-aids, gauze, or other means applied onto a wound, from which they are transferred to the wound area. Such devices also include slow-release devices, continually releasing plasminogen or other components for a prolonged period of time. With respect to healing of tympanic membranes, administration of the composition using a gel, spray, or drop-wise application via the outer ear canal, is one preferred embodiment. Injectable dosage forms or infusions comprise a solution of plasminogen or plasmin in a pharmaceutically acceptable liquid such as, e.g., isotonic saline, sterile water, or aqueous buffer systems.

After pharmaceutical compositions have been prepared, they can be placed in an appropriate container and labeled for treatment of an indicated condition. For administration of a composition of the invention, such labeling would include amount, frequency, and method of administration.

The administration of plasminogen can be repeated at least once. For example, plasminogen could be administered at regular intervals, e.g., at least about once per second day, about once a day, or about twice a day, or added in wound dressings or slow-release devices which are changed as appropriate.

Animal Models

Novel methods to screen for or evaluate candidate compounds or treatment methods that improve the healing of wounds are provided. Because of the concise structure and high similarity with skin tissue, tympanic membranes provide a unique opportunity to study the general mechanisms of wound healing. Perforations of a standardized size can be performed and the healing pattern followed by various techniques, e.g., in the otomicroscope and light microscope (Hellström et al., In: Fidia Research Series, Vol. 8, Liviana Press, Padova 1989). Thus, drug testing and screening for compounds increasing the wound concentration of plasminogen, as well as dosages and administration routes, can advantageously be studied in such animal models. The animal models of the invention also provide for drug screening for conditions where the healing process is slow or inhibited.

In accordance with the present invention, wild-type or plasminogen-deficient mice can be used to screen for compounds that improve wound healing and/or reduce scar formation. A compound for treatment of wounds, as well as diseases and conditions associated with ECM degradation, has been identified and verified using this model. However, also wild-type animals, as well as other gene-deficient animals could be used in the context of this model.

The animals used in these methods may be wild-type experimental animals conventionally used in the art, or may be genetically modified animals or "transgenic" animals. Transgenic mammals can be prepared by any method, including but not limited to modification of embryonic stem (ES) cells and heteronuclear injection into blast cells. Particularly preferred animal models include homozygous or heterozygous plasminogen-deficient mice (see, e.g., Ploplis et al. Circulation 92, 2585-2593 (1995)). As an example, plasminogen was identified as a compound improving wound healing and reducing scar formation as described in the Examples.

For example, a "knockout mammal" is a mammal (e.g., mouse) that contains within its genome a specific gene that has been inactivated by the method of gene targeting (see, e.g., U.S. Pat. Nos. 5,777,195 and 5,616,491). A knockout mammal includes both a heterozygote knockout (i.e., one defective allele and one wild-type allele) and a homozygous mutant. Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou et al. (Genes and Development 9:2623-34 (1995)) describe PPCA knock-out mice, and the Examples provided herein describe animals in which one or both alleles of plasminogen have been knocked-out.

A "knock-in" mammal is a mammal in which an endogenous gene is substituted with a heterologous gene (Roemer et al., New Biol. 3:331-5 (1991)). Preferably, the heterologous gene is "knocked-in" to a locus of interest, either the subject of evaluation (in which case the gene may be a reporter gene; see Elegant et al., Proc. Natl. Acad. Sci. USA 95:11897 (1998)) of expression or function of a homologous gene, thereby linking the heterologous gene expression to transcription from the appropriate promoter. This can be achieved by homologous recombination, transposon (Westphal and Leder, Curr Biol 7:530 (1997)), using mutant recombination sites (Araki et al., Nucleic Acids Res 25:868 (1997)) or PCR (Zhang and Henderson, Biotechniques 25:784 (1998)). In the context of the invention, human plasminogen can be "knocked-in" instead of the CIA mouse counterpart to study the effects of a drug directed against any of these drug targets.

In another series of embodiments, transgenic animals can be created in which (i) a human plasminogen gene is stably inserted into the genome of the transgenic animal; and/or (ii) the endogenous corresponding genes are inactivated and replaced with their human counterparts (see, e.g., Coffman, Semin. Nephrol. 17:404 (1997); Esther et al., Lab. Invest. 74:953 (1996); and Murakami et al., Blood Press. Suppl. 2:36 (1996)). Such animals can be treated with candidate compounds and monitored for wound healing or level/activity of plasminogen or plasmin.

Transgenic animals based on the tympanic membrane perforation model can be prepared for studying new drug targets for wound healing, or for evaluating potential drugs affecting the healing of wound diseases Such animals provide excellent models for screening or testing drug candidates. Human plasminogen-activation "knockout" animals can be prepared to identify novel drug targets as described in the Examples, and "knock-in" mammals can be prepared for evaluating drug effects on human counterparts of the plasminogen-activation system. Both technologies permit manipulation of single units of genetic information in their natural position in a cell genome and to examine the results of that manipulation in the background of a terminally differentiated organism.

Because of the concise structure and high similarity with skin tissue, tympanic membrane perforations provide a unique opportunity to study the general mechanisms of wound healing. The tympanic membrane is an extremely standardized model that gives very well defined wounds since it has an exact and very defined composition. It has 3 layers and one of the layers are composed of 5-6 keratinocytes depth; the middle layer is a connective tissue layer composed with very thin collagen II, the mucosal inner layer is made of epithelium cells. Thereby, wound healing can be studied at a cellular level. By contrast, in the case of skin wound, it may be difficult to evaluate and standardize the depth of the wound.

Screening Methods

The tympanic membrane healing model, using wild-type, plasminogen-deficient, or other gene-deficient animals, can be used as models to screen for compounds that have an effect on wound healing, allowing monitoring of the inflammatory phase (which can last about 3 days after perforation), and the subsequent tissue formation and remodeling phase. This animal model is especially advantageous for screening for active agents that accelerate wound healing or reduce scar formation. As shown in the Examples, the addition of plasminogen to plasminogen-deficient mice had a pronounced effect on tympanic membrane healing and reduced scar formation, whereas no addition of plasminogen resulted in slow or no healing and pronounced scar formation in the tympanic membrane.

By using wild type mice different compounds could be applied at the same time as the perforation is made and the healing pattern could be followed by oto-microscopically and by morphological analysis. On one side the tympanic membrane is treated with compound and the other side is used as control and treated with saline. If different gene deficient mice with defect wound healing for example plasminogen deficient mice are used, different compounds that can substitute for the lacking gene product can be found. If such compound is applied the mouse would heal also in the absence of a gene product. In that way compounds that affect steps down streams can be found.

If normal wild-type mice are used, the tympanic membrane perforation model could be used to develop drugs that accelerate wound healing. Mice could be treated with the compound to be tested and tympanic membrane healing could be monitored and compared with controls. Preferably, the drug or active agent interferes with a component of the plasminogen-activation pathway so that the level of plasminogen in the wound area is increased. One non-limiting example of compounds that could be screened for their effect on wound-healing is growth factors.

Alternatively, plasminogen deficient mice that should have abnormal wound healing could be used and wound healing could be studied by inducing a standardized wound size. The mice could also be given a potential compound to be tested. If the mice develop proper wound healing, the tested compound interferes with or targets some component that is important for wound healing. In a preferred embodiment, the drug is plasminogen or a plasminogen derivative (mutant, fragment, etc.). In another embodiment, the drug compensates for the lack of plasminogen, thereby enhancing wound healing.

In another embodiment, the mice are deficient with respect to at least one other component of the plasminogen-activation system, or for one or more MMP's. For this purpose tPA, uPA, uPA receptor, PAI-1, MMP-9, Stromolysin-3 deficient mice can be prepared as described herein.

The invention also provides a transgenic non-human animal assay system which provides a model system for testing for an agent that accelerate proper wound healing by activating the expression or activity of a drug target such as plasmin or plasminogen. Such a system comprises: (a) inducing a wound, preferably a perforation of the tympanic membrane; (b) administering the test agent to selected wild-type or transgenic non-human animal (the agent may also be administered before infliction of the wound); (c) determining whether said agent enhances wound healing and/or reduces scar formation in the wild-type or transgenic non-human animal relative to a wild-type or transgenic non-human animal of step (a) to which the agent has not been administered.

The agent may be administered to the animal by any suitable administration mode described herein, such as, e.g., topical application and intravenous injection. The administration schedule and dosages can be individually determined based on knowledge in the art of suitable schedules and amounts, or may be determined experimentally by evaluating the effect on wound healing of a range administration schedules and dosages, without undue experimentation.

If the administration of the agent decreases the time for wound healing and/or reduces scar formation, the agent may be used for enhancing wound healing according to the method of the invention. The agent may also be incorporated in a pharmaceutical composition as described herein.

An agent used in the method of the invention preferably enhances wound healing by enhancing the levels or activity of plasminogen or plasmin in comparison to a control or reference. The control or reference may be, e.g., a predetermined reference value, or may be evaluated experimentally. The agent may bind to or otherwise interfere with either one of these components. For example, in a cell-based assay where a host cell expressing recombinant plasminogen is incubated in a medium containing a potential modulating agent, a control or reference may be, e.g., a host cell incubated with an agent having a known effect on the expression or activity of the drug target protein, a host cell incubated in the same medium without any agent, a host cell transfected with a "mock" vector not expressing any drug target protein, or any other suitable control or reference. In a cell-free assay where the drug target protein or fragment is incubated in a medium containing a potential modulating agent, a control or reference may be, for example, medium not containing the drug target, medium not containing any agent, medium containing a reference polypeptide or agent, or any other suitable control or reference.

EXAMPLES

The invention is further described by means of the following examples. However, these examples are only illustrative of the invention, and in no way limits the scope and meaning of the invention. Indeed, many modifications and variations of the invention will be apparent to those skilled in the art upon reading this specification, and can be made without departing from its sprit and scope.

Example 1

Healing of Disrupted Tympanic Membranes in Wild-Type and Plasminogen-Deficient Mice This Example shows that plasminogen-deficient mice had delayed and abnormal wound healing compared to wild type control siblings. Short term studies between plasminogen deficient and wild type control mice showed from as early as 6 hours after perforation performed, plasminogen deficient mice had much higher inflammatory response indicating plasminogen function as early as the inflammation stage of wound healing.

Methods

Mice.
Adult male plasminogen gene deficient and wildtype sibling mice (C57BL/6J, 8-12 week old) were genotyped by a chromogenic activity assay, which determines the level of plasminogen in mouse plasma (Ny et al., Endocrinology. 140(11):5030-5 (1999)) and confirmed with PCR. The mice were anesthetized and under an otomicroscope their tympanic membranes were perforated with a myringotomy lancet. The perforation occupied the upper posterior quadrant of the tympanic membrane.

Genotyping of the Animals with PCR.

Genomic DNA was isolated from mouse tail tips and genotyped by PCR. The sequences of the primer pairs used in the PCR reaction were as follows:

```
neo:
                                      (SEQ ID NO:2)
    5' ATG ATT GAA CAA GAT GGA TTG CAC G 3'

(SEQ ID NO:3)
    5' TTC GTC CAG ATC ATC CTG ATC GAC 3' plg:
                                      (SEQ ID NO:4)
    5' TCA GCA GGG CAA TGT CAC GG 3'

(SEQ ID NO:5)
    5' CTC TCT GTC TGC CTT CCA TGG 3'
```

"Neo" means neomycin, which is the resistance marker used for the development of gene deficient mice. The neo gene is added to the genome as a "bullet" to inactivate the gene. A gene deficient cell therefore lacks the intact gene but has the neo gene inserted instead.

PCR was performed by standard procedure. Briefly, an initial denaturation at 94 C for 3 min followed by 30 cycles of denaturation at 93° C. for 30 seconds, annealing at 55° C. for 30 seconds, and elongation at 72° C. for 45 seconds, and finally followed by a 5 min elongation at 72° C.

Genotyping of the Animals with Chromogenic Assay.

To assay the plasminogen level in mouse plasma urokinase (ukidan) was added and the amount of plasmin formed was determined. By comparing the amount of generated plasmin between the different plasma samples the genotype of a mouse could be determined. Briefly, blood was collected from the mouse tail-tip in the presence of 0.04 M citric acid. Plasma was prepared by centrifuging for 10 min at 3000 rpm and was kept at −20° C. until the experiment was performed. Mouse plasma, diluted 1000 times was incubated with 65 nM urokinase, 10 mM lysine and 80 uM chromogenic substrate S-2251 in PBS at 37° C. in a plate (96 well) with a total volume of 200 µl/well. S-2251 becomes colored when cleaved by a proteinase. Individual sample blanks, to compensate for different colors of the plasma samples, were identical to the sample with the exception that urokinase was excluded. Absorbance was measured at 405 nm every 30 min for 2 h with a microtitertek plate reader. The average increase in absorbance over time was calculated for each mouse. The three different genotypes could be distinguished on three different levels of average increase in absorbance over time, high (plg+/+), medium (plg+/−) and low (plg−/−).

Clinical Evaluation of Wound Healing and Histological Preparations.

Wound healing appearance was evaluated under otomicroscope at 4, 8, 36, 72, and 144 days after perforation, respectively. At each time point, mice were decapitated, their tympanic bullas were cleaned from soft tissue, opened and put into 2% glutaraldehyde in cacodylate buffer overnight. The tympanic membrane, including pars tensa and pars flaccida, was dissected, rinsed and postfixed in osmium tetroxide. After dehydration in acetone, the specimens were embedded in a epoxy resin. The plastic embedded tympanic membranes were sectioned parallel to the handle of the malleus through the perforated quadrant. The toluidine-blue stained, 0.5 micron sections were then examined in the light microscope. Ultra-thin sections, 700 nm in thickness, were also cut and contrasted with uranyl acetate and lead citrate and then studied in the electron microscope.

Results

The healing of tympanic membrane was impaired in plasminogen deficient mice, as revealed by histological and morphological examination (see Table 2). Table 2 shows the results from the evaluation of the otomicroscopical appearance of the tympanic membrane, as a function of time after perforation. The numbers of overtly closed tympanic membranes are given in relation to the total number examined. Morphological analysis revealed the wild type mice perfectly healed, however, all the perforations in plasminogen deficient mice had totally disrupted healing pattern compared to wild-type.

TABLE 2

Healing of tympanic membrane is permanently impaired in plasminogen deficient mice
The table shows the fraction of overtly covered tympanic membranes in each group at each time point.

| | Time after perforation (days): | | | | | |
|---|---|---|---|---|---|---|
| | 4 | 8 | 11 | 36 | 72 | 144 |
| Plasminogen-deficient mice: | 2/24 | 6/14 | 0/6 | 1/6 | 8/30 | 0/12 |
| Wild-type mice: | 0/18 | 10/14 | 10/10 | 10/10 | 24/24 | 12/12 |

In addition, data from the healing of mice that are heterozygote for the plasminogen gene data were evaluated. These mice have 50% of the plasminogen concentration in their body fluids and they were found to have a retarded healing as compared to wild type mice. This shows that the healing process is dose-dependent and thus that administration of plasminogen to wild-type mice and humans could speed up the healing process.

Example 2

Tympanic Membrane Healing in Plasminogen-Deficient Mice Reconstituted with Plasminogen This Example demonstrates that by reconstitution of plasminogen in plasminogen deficient mice by systemic administration, the phenotype was converted completely back to normal wound healing.

Methods

This experiment was performed in a similar manner as Example 1, except for administration of plasminogen to one group of animals.

Reconstitution of Plasminogen in Plasminogen Deficient Mice.

Human plasminogen was reconstituted in plasminogen-deficient mice by repeated intravenous injections of 1.5 mg plasminogen in 100 µl phosphate-buffered saline (PBS). The first dose was administered 12 hours prior to perforation of the tympanic membrane. Thereafter, plasminogen was administered every 24 hours throughout the duration of the experiment.

Results

Reconstitution of plasminogen in plasminogen deficient mice by i.v. injection restored the normal wound healing in plasminogen deficient mice. Table 3 shows the results from the evaluation of otomicroscopical appearance of the tympanic membrane after healing. The number of healed tympanic membranes are given in relation to the total number examined.

TABLE 3

Tympanic membrane healing in Plg deficient mice after Plg administration. The table shows the fraction of healed tympanic membranes in each group at each time point.

| | Time after perforation (days): | | |
|---|---|---|---|
| | 4 | 8 | 11 |
| Plg$^{-/-}$ mice: | 0/3 | 0/3 | 0/3 |
| Wild type mice: | 0/3 | 2/3 | 3/3 |
| Plg$^{-/-}$ injected with plg: | 0/3 | 2/3 | 3/3 |

Thus, in plasminogen deficient mice wound healing of the tympanic membrane is abnormal, whereas healing of the tympanic membrane is restored in plasminogen deficient mice after administration of plasminogen. In addition, after 144 days, none of the plasminogen deficient mice had normally healed tympanic membranes, the healing pattern was completely aberrant in that the tympanic membrane became thick and non-transparent, with whitish cobble-stone like tissue covering the wound area. Morphology analysis revealed that the tissue filling up the wound area had a fibrin-like structure, indicating that cell migration had been hindered. Necrosis was apparent from Day 16 and onwards.

Example 3

Healing of Tympanic Membrane Perforations in tPA-Deficient Mice

Tympanic membranes (TM) of tPA-deficient (tPA$^{-/-}$) and wild-type mice were perforated at day 0, and the healing pattern was followed under otomicrocope, as described above. The results are described in Table 4. tPA-deficient mice back-crossed 6 times to C57Bl/6 background were crossed once to DBA1/J background. The heterozygous litters were used for breeding. The wild-type (tPA$^{+/+}$) and homozygous (tPA$^{-/-}$) offspring from these breedings were used in the wound-healing experiments.

TABLE 4

Healing Of Tympanic Membranes In tPA-Deficient Mice.
The table shows the fraction of healed tympanic membranes in each group at each time point.

| | Time after perforation (days): | | | |
|---|---|---|---|---|
| | 4 | 6 | 8 | 12 |
| tPA$^{+/+}$ mice: | 0/20 | 5/14 | 9/14 | 6/6 |
| tPA$^{-/-}$ mice: | 0/24 | 4/16 | 10/16 | 8/8 |

The healing pattern of TM perforation in tPA$^{-/-}$ mice was identical to that of wild type control mice, and the quality of healed TM tissue in tPA$^{-/-}$ mice and wild type controls appeared identical, in that no "cobble-stone-like" tissue or fibrin deposits could be observed in the wound area. Accordingly, no significant quantitative or qualitative differences in tympanic membrane healing were observed in tPA-deficient mice as compared to wild-type, thereby indicating that tPA plays a lesser, if any, role in tympanic membrane healing.

Example 4

Healing of Tympanic Membrane Perforations in uPA-Deficient Mice

Tympanic membranes in wild-type and uPA-deficient (uPA$^{-/-}$) mice were perforated at day 0, and the healing pattern monitored by otomicrocope as described above. The results are set forth in Table 5. uPA-deficient mice backcrossed 6 times to C57B1/6 background were crossed once to DBA1/J background. The heterozygous litters were used for breeding. The wild-type (uPA$^{+/+}$) and homozygous (uPA$^{-/-}$) offspring from these breedings were used in the wound-healing experiments.

TABLE 5

Healing Of Tympanic Membranes In uPA-Deficient Mice.
The table shows the fraction of healed tympanic
membranes in each group at each time point.

| | Time after perforation (days): | | | |
|---|---|---|---|---|
| | 4 | 8 | 16 | 30 |
| Wild-type mice: | 0/12 | 5/8 | 8/8 | 6/6 |
| uPA$^{-/-}$ mice: | 0/16 | 5/12 | 7/8 | 3/4 |

This experiment showed that healing of tympanic membrane perforation in uPA-deficient mice was somewhat delayed as compared to wild type controls, and whitish and cobble-stone-like tissue, with fibrin depositions, could be observed in the perforated area after healing. These data suggest that uPA may play a role in the tympanic membrane or wound healing process, potentially affecting the clearance of fibrin depositions, although to a lesser degree than plasminogen.

Example 5

"Late" Administration of Plasminogen

This example shows that an impaired healing process can be restored by the administration of plasminogen several weeks after the tympanic membrane perforation was inflicted.

Methods.

Plasminogen-deficient (plg−/−) mice were prepared as described above. The tympanic membranes were perforated at Day 0. On day 36 and onwards for 7 days, one group of the plg−/− mice were injected daily with 1.5 mg human plasminogen in 150 μl solution.

Results.

A reduction of the abnormally accumulated extracellular matrix due to administration of plasminogen could be detected by otomicroscopy. Specifically, in the plasminogen-deficient mice that received daily administrations of human plasminogen, an inflammatory reaction started which resulted in an exudation of accumulated material from the tympanic membrane area within 2 days after the first administration. During the 7-day injection period, these mice showed greatly diminished thickness of the abnormally accumulated extracellular matrix (mainly consisting of fibrin and necrotic tissue). After this initial 7-day period, the healing pattern of some tympanic membranes resembled that of normal healing. These results indicate that plasminogen is essential for the fibrin clearance and removal of necrotic tissue.

In a similar plasminogen restoration experiment, plasminogen deficient mice received plasminogen during either days 0-3, days 4-7 or days 8-11 after the perforation. This experiment showed that plasminogen was important during all three stages of the wound healing: the inflammatory stage, the tissue formation stage and the tissue remodeling stage.

Example 6

Topical Application of Plasminogen on Perforated Tympanic Membranes in Wild-Type Rats This example shows that healing of tympanic membrane perforations is improved in wild-type rats by local application of plasminogen.

Methods.

Ten tympanic membranes per animal study group were punctured. Fifty μl of PBS (control) or human plasminogen at a concentration of 1 mg/ml or 10 mg/ml was applied directly onto the tympanic membrane perforation. The addition of plasminogen or control was repeated every 24 hours, and the inflammatory reaction and healing pattern were monitored at different time points. Specifically, the accumulation of inflammatory fluid in the midear cavity was followed at the attic area, and the shrinkage of the TM perforations were followed during the first 108 hours after the perforations.

Results.

The mean healing time in each group was followed and is shown in Table 6 below. The table shows the average time period for healing of a tympanic membrane perforation for each group.

TABLE 6

Improvement of Healing of Tympanic Membrane Perforations
In Wild-Type Rats by Administration of Plasminogen

| | Group: | | |
|---|---|---|---|
| | Control (PBS) | 1 mg/ml Plg | 10 mg/ml Plg |
| Time to Healing (days): | 8.1 ± 0.5 | 7.4 ± 0.6 | 6.8 ± 0.5 |

The rats that received 10 mg/ml of plasminogen had the strongest inflammatory reaction in the attic area of the midear, while rats that received 1 mg/ml plasminogen displayed an almost similar inflammatory reaction as controls. The fastest healing of tympanic membranes was observed in the 10 mg/ml group, although both groups receiving plasminogen showed an improved shrinkage of the perforation during the first 108 hours as compared to controls.

Example 7

Characterization of Tissue Remodeling and Cell Migration Events in Plasminogen-Deficient Mice In order to characterize the abnormal tissue remodeling and cell migration events in plasminogen-deficient (plg$^{-/-}$)

mice, serial immunostainings of keratin, fibrin and neutrophils were conducted on healing/healed tympanic membranes from wild-type and plg−/− mice at days 4, 8, 16, 36, 72 and 144 after perforation. The neutrophil-reactive antibody was from Cedarlane (Canada), the anti-keratin antibody was from ICN Pharmaceuticals, Inc., and the fibrinogen/fibrin-reactive antibody was from Nordic Immunology.

Results.

At day 36 and onwards after the perforation, plasminogen-deficient mice had an abnormal extracellular matrix composition compared to wild type mice. In the plasminogen-deficient mice, the perforations contained increased amounts of fibrin instead of keratin, while keratin was "kept" at the perforation border. Under otomicroscope, these fibrin deposits are seen as whitish, "cobble-stone-like" crust tissue. Large amounts of neutrophils had also infiltrated into the wounded area. Furthermore, necrotic tissue was apparent in all plasminogen-deficient mice at day 16 after perforation and onwards. The wild-type mice displayed a healed wound area identical to normal wild-type controls.

These data suggest that plasminogen, either directly or via the formation of plasmin, is important for preventing or reducing fibrin depositions, promoting keratin layer formation, as well as removing necrotic tissue.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Numerous references, including patents, patent applications, figures, database references, and various publications, are cited and discussed in the description of this invention. All of these references are incorporated herein by reference in their entirety and to the same extent as if each reference was individually incorporated by reference.

What is claimed is:

1. A method of accelerating wound healing in a subject with an epidermal tissue wound comprising:
   administering, by subcutaneous or intramuscular injection, locally in proximity to the wound, a composition containing an amount of purified plasminogen effective to accelerate healing of the wound.

2. The method of claim 1, wherein the wound is a chronic wound.

3. The method of claim 1, wherein the subject is a human, and the plasminogen is human plasminogen.

4. The method of claim 1 wherein said composition comprises recombinant plasminogen.

\* \* \* \* \*

SEQUENCE LISTING

```
<160> NUMBER OF SEQ ID NOS: 5

<210> SEQ ID NO 1
<211> LENGTH: 810
<212> TYPE: PRT
<213> ORGANISM: Homo sapiens
<300> PUBLICATION INFORMATION:
<308> DATABASE ACCESSION NUMBER: GenBank / 625234
<309> DATABASE ENTRY DATE: 2000-09-15
<313> RELEVANT RESIDUES: (1)..(810)

<400> SEQUENCE: 1

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205
```

```
Trp Asp Ser Gln Ser Pro His Ala His Gly Tyr Ile Pro Ser Lys Phe
    210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                245                 250                 255
Cys Asp Ile Pro Arg Cys Thr Thr Pro Pro Ser Ser Gly Pro Thr
            260                 265                 270
Tyr Gln Cys Leu Lys Gly Thr Gly Glu Asn Tyr Arg Gly Asn Val Ala
        275                 280                 285
Val Thr Val Ser Gly His Thr Cys Gln His Trp Ser Ala Gln Thr Pro
    290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
            340                 345                 350
Asp Ser Ser Pro Val Ser Thr Glu Gln Leu Ala Pro Thr Ala Pro Pro
        355                 360                 365
Glu Leu Thr Pro Val Val Gln Asp Cys Tyr His Gly Asp Gly Gln Ser
    370                 375                 380
Tyr Arg Gly Thr Ser Ser Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
        435                 440                 445
Cys Asn Leu Lys Lys Cys Ser Gly Thr Glu Ala Ser Val Val Ala Pro
    450                 455                 460
Pro Pro Val Val Leu Leu Pro Asn Val Glu Thr Pro Ser Glu Glu Asp
465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
            500                 505                 510
His Ser Ile Phe Thr Pro Glu Thr Asn Pro Arg Ala Gly Leu Glu Lys
        515                 520                 525
Asn Tyr Cys Arg Asn Pro Asp Gly Asp Val Gly Gly Pro Trp Cys Tyr
    530                 535                 540
Thr Thr Asn Pro Arg Lys Leu Tyr Asp Tyr Cys Asp Val Pro Gln Cys
545                 550                 555                 560
Ala Ala Pro Ser Phe Asp Cys Gly Lys Pro Gln Val Glu Pro Lys Lys
                565                 570                 575
Cys Pro Gly Arg Val Val Gly Gly Cys Val Ala His Pro His Ser Trp
            580                 585                 590
Pro Trp Gln Val Ser Leu Arg Thr Arg Phe Gly Met His Phe Cys Gly
        595                 600                 605
Gly Thr Leu Ile Ser Pro Glu Trp Val Leu Thr Ala Ala His Cys Leu
    610                 615                 620
Glu Lys Ser Pro Arg Pro Ser Ser Tyr Lys Val Ile Leu Gly Ala His
```

-continued

```
                625                 630                 635                 640
Gln Glu Val Asn Leu Glu Pro His Val Gln Glu Ile Glu Val Ser Arg
                    645                 650                 655
Leu Phe Leu Glu Pro Thr Arg Lys Asp Ile Ala Leu Lys Leu Ser
            660                 665                 670
Ser Pro Ala Val Ile Thr Asp Lys Val Ile Pro Ala Cys Leu Pro Ser
        675                 680                 685
Pro Asn Tyr Val Val Ala Asp Arg Thr Glu Cys Phe Ile Thr Gly Trp
    690                 695                 700
Gly Glu Thr Gln Gly Thr Phe Gly Ala Gly Leu Leu Lys Glu Ala Gln
705                 710                 715                 720
Leu Pro Val Ile Glu Asn Lys Val Cys Asn Arg Tyr Glu Phe Leu Asn
                725                 730                 735
Gly Arg Val Gln Ser Thr Glu Leu Cys Ala Gly His Leu Ala Gly Gly
            740                 745                 750
Thr Asp Ser Cys Gln Gly Asp Ser Gly Gly Pro Leu Val Cys Phe Glu
        755                 760                 765
Lys Asp Lys Tyr Ile Leu Gln Gly Val Thr Ser Trp Gly Leu Gly Cys
    770                 775                 780
Ala Arg Pro Asn Lys Pro Gly Val Tyr Val Arg Val Ser Arg Phe Val
785                 790                 795                 800
Thr Trp Ile Glu Gly Val Met Arg Asn Asn
                805                 810

<210> SEQ ID NO 2
<211> LENGTH: 25
<212> TYPE: DNA
<213> ORGANISM: Artificial Sequence
<220> FEATURE:
<223> OTHER INFORMATION: PCR primer

<400> SEQUENCE: 2
atgattgaac aagatggatt gcacg                                          25

<210> SEQ ID NO 3
<211> LENGTH: 24
<212> TYPE: DNA
<213> ORGANISM: Artificial Sequence
<220> FEATURE:
<223> OTHER INFORMATION: PCR primer

<400> SEQUENCE: 3
ttcgtccaga tcatcctgat cgac                                           24

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
tcagcagggc aatgtcacgg                                                20

<210> SEQ ID NO 5
<211> LENGTH: 21
<212> TYPE: DNA
<213> ORGANISM: Artificial Sequence
<220> FEATURE:
<223> OTHER INFORMATION: PCR primer
```

```
<400> SEQUENCE: 5
ctctctgtct gccttccatg g                                            21
```